US00PP25609P2

(12) United States Plant Patent
Zampini

(10) Patent No.: US PP25,609 P2
(45) Date of Patent: Jun. 2, 2015

(54) ***BERBERIS* PLANT NAMED 'MIDRUZAM'**

(50) Latin Name: *Berberis thunbergii*
Varietal Denomination: Midruzam

(71) Applicant: James W. Zampini, Fairport Harbor, OH (US)

(72) Inventor: James W. Zampini, Fairport Harbor, OH (US)

(73) Assignee: Lake Country Nursery, Perry, OH (US)

( * ) Notice: Subject to any disclaimer, the term of this patent is extended or adjusted under 35 U.S.C. 154(b) by 192 days.

(21) Appl. No.: 13/815,636

(22) Filed: Mar. 13, 2013

(51) Int. Cl.
*A01H 5/12* (2006.01)

(52) U.S. Cl.
USPC ..... Plt./241

(58) Field of Classification Search
USPC ..... Plt./241
See application file for complete search history.

(56) References Cited

PUBLICATIONS

Code of Federal Regulations, vol. 5, Jan. 1, 2010, Title 7—Agriculture.*

* cited by examiner

*Primary Examiner* — Anne Grunberg
(74) *Attorney, Agent, or Firm* — Penny J. Aguirre

(57) ABSTRACT

A new cultivar of *Berberis*, 'Midruzam', characterized by its low growing, compact, and rounded plant habit, its very slow growth habit, its foliage that is dark burgundy in color in summer and turns red in color in the fall, and its lack of flower and fruit production.

2 Drawing Sheets

Botanical classification: *Berberis thunbergii.*
Variety denomination: 'Midruzam'.

BACKGROUND OF THE INVENTION

The present invention relates to a new and distinct cultivar of *Berberis thunbergii* and will be referred to hereafter by its cultivar name, 'Midruzam'. 'Midruzam' is a new cultivar of shrub grown for use as an ornamental landscape plant.

The Inventor discovered the new cultivar as a chance seedling that was growing in a container at his nursery in Perry, Ohio in 2009. The parent plants are therefore unknown.

Asexual propagation of the new cultivar was first accomplished by the Inventor using softwood stem cuttings in summer of 2009 in Perry, Ohio. Asexual propagation of the new cultivar by softwood stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'Midruzam' as unique cultivar of *Berberis.*

1. 'Midruzam' exhibits a low growing, compact, and rounded plant habit.
2. 'Midruzam' exhibits a very slow growth habit.
3. 'Midruzam' exhibits foliage that is dark burgundy in color in summer and turns red in color in the fall.
4. 'Midruzam' has not been observed to produce flowers or fruit.

'Midruzam' can be most closely compared to the cultivars 'Pygruzam' (not patented), and 'Gentry' (U.S. Plant Pat. No. 9,461). Both cultivars differ from 'Midruzam' in having less compact and more open plant habits, leaves that are smaller in size and light in color, and in producing seeds.

BRIEF DESCRIPTION OF THE DRAWING

The accompanying colored photographs were taken in mid summer and illustrate the overall appearance and distinct characteristics of 2 year-old plants the new *Berberis* as grown outdoors in a trial bed in Perry, Ohio.

The photograph in FIG. 1 provides an overall view of the plant habit and foliage coloration of 'Midruzam' in summer.

Figure 1:
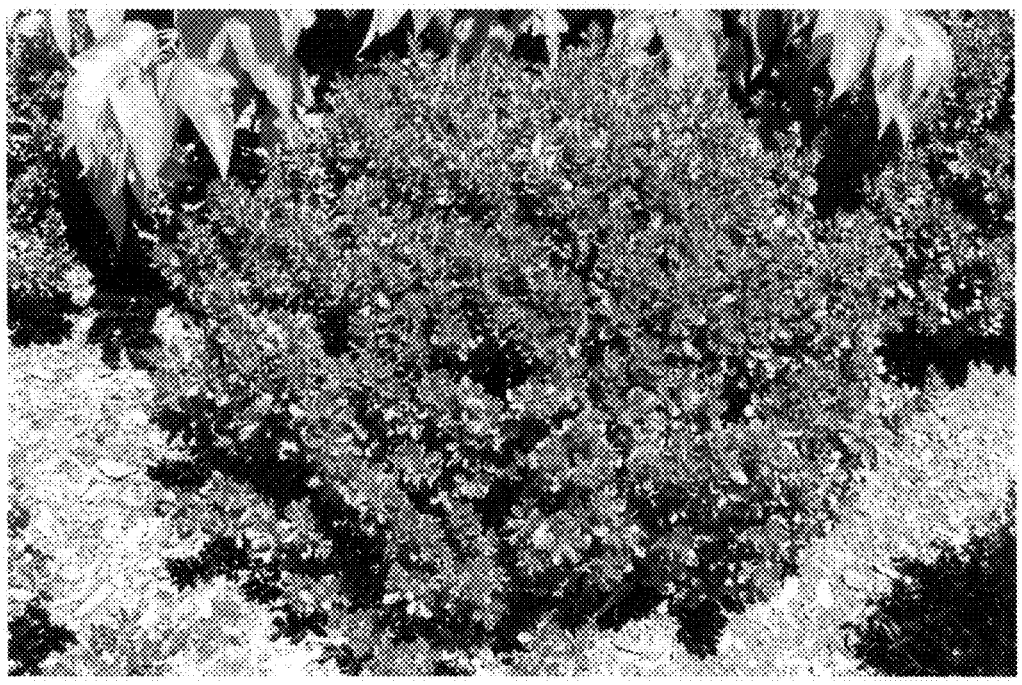
Figure 2:
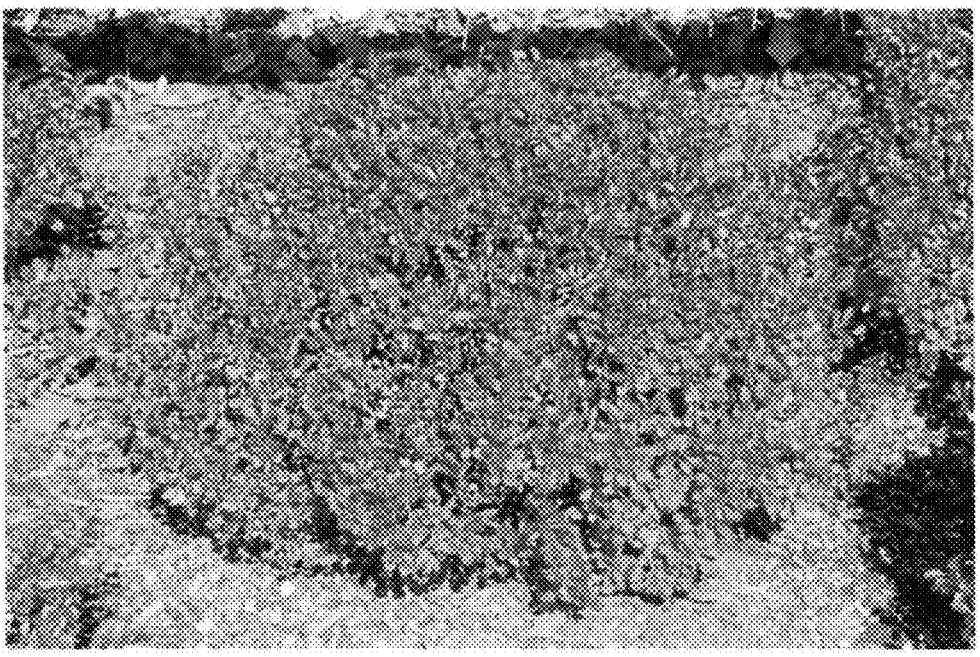

The photograph in FIG. 2 provides a view of the foliage coloration of 'Midruzam' in fall.

Figure 3:
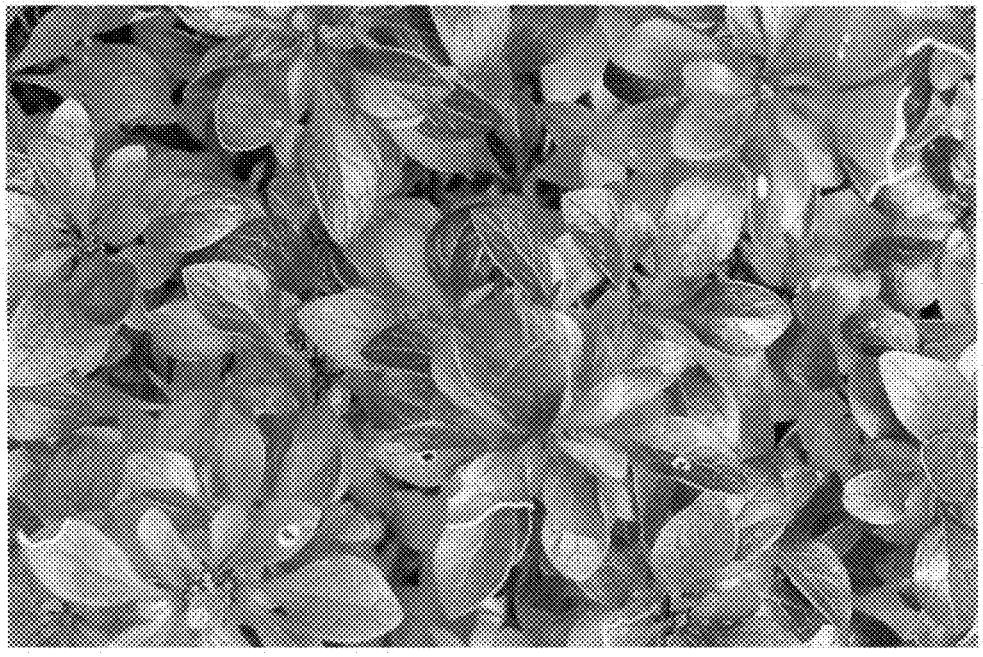

The photograph in FIG. 3 provides a close-up view of the foliage of 'Midruzam' in fall.

The colors in the photographs may differ slightly from the color values cited in the detailed botanical description, which accurately describe the colors of the new *Berberis.*

DETAILED BOTANICAL DESCRIPTION

The following is a detailed description of 2 year-old plants the new *Berberis* as grown in 3-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—No blooms have been observed.
*Plant type.*—Evergreen shrub.
*Plant habit.*—Low growing, compact, and rounded.

*Plant height and spread.*—Reaches 40 to 46 cm (16 to 18 inches) in height and about 46 cm (18 inches) in spread.

*Diseases and pests.*—The new cultivar has been observed to be disease free to date under the conditions of trials and has shown to be resistant to black stem rust.

*Sun tolerance.*—High, no foliage burning has been observed when grown in full sun with sufficient moisture.

*Cold hardiness.*—At least in U.S.D.A. Zone 4.

*Root description.*—Fibrous.

*Propagation*—Softwood stem cuttings.

*Growth rate.*—Very slow.

Stem description:

*Shape.*—Round.

*Stem color.*—New growth; 175A, maturing; N144A, mature bark ; a blend of 200C and 161C.

*Stem size.*—Main branches; about 12 cm in length and 4 mm in diameter, lateral branches; average of 17 cm in length and 2.5 mm in diameter.

*Stem surface.*—New growth; glabrous and slightly glossy, mature wood is dull and smooth and becoming bark-like as it ages.

*Internode length.*—Average of 7 mm.

*Branching.*—An average of 6 lateral branches per mature stems with numberous basal stems ariseing from base; about 15 in a one-gallon container.

Foliage description:

*Leaf shape.*—Elliptic to obovate to spatulate (due to acuminate base).

*Leaf division.*—Simple.

*Leaf base.*—Long attenuate.

*Leaf apex.*—Broadly acute.

*Leaf venation.*—Pinnate.

*Leaf margins.*—Entire.

*Leaf attachment.*—Sessile.

*Leaf arrangement.*—Alternate.

*Leaf surface.*—Smooth and moderately glossy on upper and lower surface.

*Leaf internode length.*—Average of 3 mm between nodes, whorls of 1 to 6 leaves at axils.

*Leaf size.*—Up to 4 cm in length and 1.5 cm in width when mature.

*Leaf quantity.*—Average of 40 pair per branch 15 cm in length on new lateral branches.

*Leaf color.*—Newly expanded leaves upper surface; a blend of N77A and 178A, newly expanded leaves lower surface; N138B and slightly suffused with 178A, mature leaves upper surface; 137A to 138B and suffused with N77A becoming 137A to 137B, mature leaves lower surface; 138B, fall leaves upper surface; 187A and 43A, fall leaves lower surface; 138A and suffused with either 187A or 43A.

*Thorns.*—Below each node is a sharp single thorn; average of 7 mm in length and 1 mm in width at base, 166A in color.

Inflorescence and fruit description: No flowers or fruit have been observed to date on the new cultivar.

It is claimed:

1. A new and distinct cultivar of *Berberis* plant named 'Midruzam' as herein illustrated and described.

* * * * *